's Patent Number: 5,098,830
Date of Patent: Mar. 24, 1992

United States Patent [19]
Bar-or et al.

[54] VERY RAPID DETECTION OF FUNGAL INFECTIONS

[75] Inventors: David Bar-or; Clive Solomons, both of Denver, Colo.

[73] Assignee: Diagnostic Markers, Inc., Englewood, Colo.

[21] Appl. No.: 554,003

[22] Filed: Jul. 16, 1990

[51] Int. Cl.⁵ .................. C12Q 1/28; C12Q 1/44; C12Q 1/02; C12Q 1/04
[52] U.S. Cl. ........................... 435/28; 435/34; 435/19; 435/30; 435/29
[58] Field of Search ............ 435/28, 2, 19, 30, 34, 435/29; 424/10, 60; 514/567; 436/514

[56] References Cited

U.S. PATENT DOCUMENTS

| | | | |
|---|---|---|---|
| 4,021,538 | 5/1977 | Yu et al. | 424/60 |
| 4,140,580 | 2/1979 | Gibson et al. | |
| 4,728,607 | 3/1988 | Dorn et al. | |
| 4,847,128 | 7/1989 | Dorn et al. | |
| 4,874,695 | 10/1989 | Dincus | 435/19 |

OTHER PUBLICATIONS

David (1980) Microbiology, pp. 833–835, Harper & Row, Philadelphia.
Chaskes et al. (Jun. 81) ADL-DOPA Drug Test for the Identification of Cryptococcus Neoformans, Mycopathologia, 74(3) pp. 143–148.
Huxham et al. (1986) A simple usual method for assessing the actuation . . . insect haemocytes in vitro, J Immo. Meth 94: 271–7.

*Primary Examiner*—Robert A. Wax
*Assistant Examiner*—David R. Preston
*Attorney, Agent, or Firm*—Darby & Darby

[57] ABSTRACT

A method for the detection of a fungal infection within 1–2 hours comprises the steps of: (a) contacting a sample suspected of containing a peroxidase-containing fungus with a mixture which comprises (i) a peroxide from hydrogen peroxide and addition compounds thereof containing latent hydrogen peroxide; (ii) a scavenger to remove heavy metals which may potentially decompose said peroxide catalytically; (iii) an alkaline buffer solution having the capacity to maintain the pH at a value within the range of 9.5 to 14; and (iv) a colorless oxidizable substrate (such as tyrosine, β-(3,4-dihydroxyphenyl)-α-alamine (DOPA) or caffeic acid), which on reaction with oxygen at said pH value gives a visibly colored oxidation product; and (b) observing whether a color develops indicating the presence of peroxidase-containing fungus in the sample. Also included is a test kit for carrying out the method of the invention.

26 Claims, No Drawings

VERY RAPID DETECTION OF FUNGAL INFECTIONS

FIELD OF THE INVENTION

The present invention relates to a very rapid method for the detection of fungal infections, and to a kit for use in such method.

BACKGROUND OF THE INVENTION

In gynecological practice, vaginitis is one of the major reasons for visits by patients to medical practitioners. Vaginitis caused by fungi, particularly by *Candida Albicans*, may affect 5-40% of the female population attending medical practices or clinics. Fungal infections of this nature are encouraged by any change in the normal vaginal flora, and such change may in turn be linked with such factors as variation in ovarian hormonal activity and individual broad spectrum antibiotic therapy. The diagnosis and treatment of such infections is largely based on clinical symptoms and the microscopic appearance of the vaginal discharge; the most common symptoms of vulvo-vaginitis, in particular, are intense itching an burning, accompanied by skin erosions and sometimes satellite pustules. Clinical suspicion may be confirmed by elaborate and time consuming culturing techniques.

In U.S. Pat. No. 4,874,695, which issued Oct. 17, 1989 to Pincus, a method for identification of fungal microorganisms characterized as "rapid" involved culturing the microorganisms for 2-3 days, preparing an inoculum from the culture, mixing the inoculum with a chromogenic substrate (or separately with more than one such substrate) for detecting the presence or absence of one or more of acetate esterase, leucylglycine aminopeptidase and glycylglycine aminopeptidase by formation of a colored product or a product convertible to a colored product, and incubating the inoculum/substrate mixture(s) for 2-6 hours, whereby the unknown microorganism is identified by comparing with the enzyme activity of known genera and species. Thus, the overall procedure takes 2-3 days plus 2-6 hours. The entire contents of U.S. Pat. No. 4,874,695, including the literature and patent references therein, are expressly incorporated herein by reference.

A method for detecting Candida yeasts, *Saccharamyces cerevisiae*, *Torulopsis glabrata* and *Aspergillus niger*, in which the microorganism in question is grown in a medium containing sources of nitrogen and carbon, and chloramphenicol and potassium tellurite (to inhibit the growth of gram-positive and gram-negative organisms), as well as a biological pH indicator which changes color as the medium becomes more acidic from metabolic activity of the microorganism, is disclosed in U.S. Pat. No. 4,140,580, which issued Feb. 20, 1979 to Gibson et al. The entire contents of this U.S. Patent are expressly incorporated herein by reference. In U.S. Pat. No. 4,140,580, it is stated that the entire test can be completed in 12-18 hours, compared with the then current 36-48 hours.

Other known methods are the so-called gold standard diagnosis which employs culturing in different media; and a method using monoclonal antibodies plus latex agglutination. In a well-established method, potassium hydroxide solution is applied to a smear sample on a glass slide, whereby all cells are destroyed except Candida hyphae and spores, a microscopic examination being carried out to identify the organism. This (KOH) method is, however, subjective and requires considerable laboratory skills.

SUMMARY OF THE INVENTION

It is accordingly an object of the present invention to provide a very rapid method for the detection of fungal infections; and it is a further object of the invention to provide a kit for use in such method. Other objects of the invention will be apparent from the description which follows.

The term "very rapid" in the present context means within 1-2 hours at the most.

Thus, in accordance with the present invention there is provided a method for the detection of a fungal infection which comprises the steps of:

(a) contacting a sample suspected of containing a peroxidase-containing fungus with a mixture which comprises (i) a peroxide selected from hydrogen peroxide and addition compounds thereof containing latent hydrogen peroxide; (ii) a scavenger to remove heavy metals which may potentially decompose the peroxide catalytically; (iii) an alkaline buffer solution having the capacity to maintain the pH at a value within the range of 9.5 to 14; and (iv) a colorless oxidizable substrate, which on reaction with oxygen at that pH value gives a visibly colored oxidation product; and (b) observing whether a color develops indicating the presence of peroxidase-containing fungus in the sample.

Preferably, the method of the invention also comprising the subsequent steps of:

(c) stabilizing the color by lowering the pH to the 2.4 to 3.0 range; and (d) comparing the intensity of the stabilized color with a predetermined scale for estimation of the presence and concentration of fungus in the sample.

The present invention moreover provides a test kit for use in a method for the detection of a fungal infection, due to the presence in the fungus od a peroxidase which is reactive at high alkaline pH, which comprises the following components in a container: (A) a peroxide selected from hydrogen peroxide and addition compounds thereof containing latent hydrogen peroxide;

(B) a scavenger to remove heavy metals which may potentially decompose said peroxide catalytically;

(C) an alkaline buffer solution having the capacity to maintain the pH at a value within the range of 9.5 to 14; and (D) a colorless oxidizable substrate, which on reaction with oxygen at said pH value gives a visibly colored oxidation product; and as optional additions at least one further component selected from (E), (F), (G) and (H), namely:

(E) an acid component for lowering the pH of a test mixture which includes components (A), (B), (C) and (D), and a test specimen, to the 2.4 to 3.0 range;

(F) a color scale for comparing any color which may be stabilized color which may be obtained in a test mixture which includes components (A), (B), (C), (D) and (E);

(G) a sterile swab for collecting said test specimen; and (H) a test vessel adapted for mixing at least components (A), (B), (C), (D) and said test specimen.

The oxidizable substrate comprises at least one compound selected from $\beta$-(3,4-dihydroxyphenyl)-$\alpha$-alanine (DOPA), caffeic acid, and salts thereof excepting heavy metal salts. The term "DOPA" is defined herein as meaning Dl-, D-and L-DOPA (c.f. the Merck Index, 10th edition, 1983, Monograph no. 3427 at pages 497–8).

DETAILED DESCRIPTION OF THE INVENTION

The basis of the test in accordance with a particular embodiment of the method of the invention, is the formation of melanin from L-DOPA and oxygen. Persons skilled in the art will appreciate that in its broad aspect, the invention includes using a colorless oxidizable substrate other than L-DOPA, which is capable of giving rise to a visibly colored product under the reaction conditions, which colored product may but need not include melanins. The oxygen is generated from hydrogen peroxide ($H_2O_2$) or a hydrogen peroxide addition compound such as urea/hydrogen peroxide addition compound, by the action of peroxidase present in the fungus, at a highly alkaline pH such as pH 10. The depth of color of dark colored melanin produced is proportional to the amount of fungus present in the sample undergoing the test. In order to increase the sensitivity and stability of the test and reduce its cost, three problems required solution, namely:

(i) non-enzymic decomposition of hydrogen peroxide by heavy metals, which would contribute towards false positive results;

(ii) false negative results due to bleaching of the color by excess hydrogen peroxide remaining after the color has developed;

(iii) the need for a buffer having significant capacity to maintain a high pH (e.g. 10) during the reaction and to remain stable during sterilization.

These problems were solved as follows. Heavy metal-catalyzed decomposition of hydrogen peroxide was prevented by use of a chelating agent such as ethylenediaminetetraacetic acid (EDTA) or a suitable salt thereof, e.g. the sodium salt. Bleaching by excess hydrogen peroxide was avoided by adding a suitable acid (e.g. citric acid) to the mixture after say, five minutes of color development, reducing the pH of the mixture to 2.4 to 3.0. Regarding the desirability of maintaining a high pH, it was found that a 0.1M sodium carbonate-bicarbonate buffer, which is widely used for the assay of alkaline phosphatase and is cheaper than some existing alternatives, could be used for this purpose. The sequestering agent, such as EDTA or a suitable salt thereof, can be added to the buffer solution, e.g. 9 volumes of the 0.1M buffer can be mixed with 1 volume 0.02M EDTA disodium salt in order to maintain pH 10 and to remove heavy metals.

Since hydrogen peroxide is most effective as a bleaching agent in alkaline pH, lowering the pH of the mixture to 2.4 to 3.0 after the color had developed completely, prevented bleaching from occurring even if left for several days. Citric acid, for example, can be used at 2M concentration to reduce the pH; it was found that citric acid of itself did not change the color intensity of the melanin formed during the reaction.

The more peroxidase-containing fungus present in the sample, the deeper the color. The pigment (in this example melanin) had an absorption maximum at 272 nanometers and an absorption minimum at 240 nanometers.

In order to determine the sensitivity of the test for fungal infections described herein, culturing a specimen from a patient (infected with Candida Albicans) on an "Easy-Cult" medium showed after 48 hours 10,000 organisms. The colonies were scraped from the surface of the culture medium and re-suspended in 1 c.c. of water, which thus contained 10,000 organisms. Serial dilutions of the latter gave 1 c.c. samples containing respectively 4000, 3000, 2000, 1000, 100, 20 and 10 organisms. Performing the test described herein, using L-DOPA as the colorless oxidizable substrate, on these different concentrations of organisms showed that 4000 or more organisms afforded a black color; 3000—a brown color; 2000—a dark-yellow color; and 1000 and below—a yellowish color or no color.

In order to demonstrate the specificity of the reaction utilized herein, several control experiments were carried out using L-DOPA as the colorless oxidizable substrate. The following gave negative results under the high alkaline pH conditions of the present inventive method:

leukocytes obtained from a normal cotton-tipped mouth swab;

a normal clinically negative swab of the vaginal cavity;

a swab from a normal uninfected oral cavity; and a swab from an oral cavity diagnosed as having a strep infection.

These control results support the proposition that the reaction utilized herein is specific for fungal infections and does not give a positive reaction with normal cells or with bacteria. On the other hand, swabs taken from patients with clinically diagnosed fungal infections (according to the KOH method) uniformly tested positive according to the present inventive method, in a time of 5 to 15 minutes, giving a dark brown color. Also, these positive results were obtained only at high alkaline pH, e.g. pH 10; control experiments at pH 4 and 7 gave no reaction. Moreover, horseradish peroxidase is an acidic peroxidase which gave either a minimal response or no response at pH 10, while leukocyte myeloperoxidase is also an acidic peroxidase giving negative results under the present conditions.

As an exemplary peroxide utilized in accordance with the present invention, solid urea/hydrogen peroxide adduct was found to be still colorless after 12 months storage at ambient temperature, in the presence of air, and retained an adequate level of activity to be viable in the present invention. Under these conditions, dry solid L-DOPA, either alone or admixed with urea/hydrogen peroxide adduct, also exhibited no change in color. Thus, the adduct and dry L-DOPA in the form of a powdered mixture may be used as one component of a test kit, another component being the buffer solution containing heavy metal scavenger; the two components would be mixed immediately before insertion of the test swab into the mixture. The test kit according to the invention could evidently contain a sterile swab as a third component, to be used to swab the oral or vaginal cavity, as desired.

EXAMPLE

Materials

In preparing the $Na_2CO_3/NaHCO_3$ buffer solution, the components may either be mixed together, or alternatively NaOH is reacted with $NaHCO_3$ to convert part of the latter to $Na_2CO_3$ in accordance with the equation:

$$NaOH + NaHCO_3 = Na_2CO_3 + H_2O.$$

$NaHCO_3$ (0.84 g.) is dissolved in water to make 100 ml. of 0.1M solution. The pH of this solution is adjusted to 10 by stirring in M NaOH solution (prepared by dissolving 4.0 g. NaOH in water, made up to 100 ml.) and continuously checking the pH. An approximately 0.1M solution of disodium ethylenediaminetetraacetic acid, disodium salt (MW 336.21), is prepared by dissolving this compound (0.34 g.) in water and making up to 100 ml, then adjusting the pH to 10 with M NaOH solution. The test solution ("A") of alkaline buffer containing also EDTA disodium salt as heavy metal scavenger is prepared by mixing 9 parts by volume 0.1M $Na_2CO_3$/$NaHCO_3$ solution with 1 part by volume EDTA disodium salt solution, prepared as just described. The substrate/peroxide mixture ("B") is utilized as a powder prepared from the dry ingredients, namely, 20 mg. urea/hydrogen peroxide adduct and 1.5 g. L-DOPA. A solution ("C", approximately 0.2M) of 4 g. citric acid in water, made up to 100 ml. and a sterile swab also form part of the kit.

Procedure

The solution A and powder B are mixed together and the swab containing the test specimen is added, the whole mixed and allowed to stand 5-20 minutes at room temperature; the color is compared with a pre-calibrated color chart. In order to prevent excess hydrogen peroxide and ammonia from bleaching the color, a quantity of solution C containing 12 mg. citric acid is added to reduce the pH to 2.5-3.0. Persons skilled in the art will be aware of the possibility of using reagents other than citric acid, for this purpose.

Results 20 patients known to have either a fungal or bacterial infection were tested according to the above procedure, which was found to have a specificity of 90.9% for fungal infections as well as a sensitivity of 90.9%. The accuracy of these tests in accordance with the invention was confirmed by other tests done on occasional patients presenting to the Emergency Department of Swedish Medical Center (DENVER, COLO.). The specificity of these tests appears to be due to the fact that fungal peroxidases are very active at highly alkaline pH, by contrast with other peroxidases e.g. myeloperoxidase, lactoperoxidase and different bacterial peroxidases.

While the present invention has been particularly described in accordance with certain embodiments thereof, it will be apparent to skilled persons that many variations and modifications can be made. Accordingly, the invention is not to be construed as limited to such particularly described embodiments, rather its concept, spirit and scope can be appreciated by reference to the claims which follow.

We claim:

1. A method for the detection of a peroxidase-containing fungus which comprises the steps of:
    (a) contacting a sample suspected of containing a peroxidase-containing fungus with a mixture which comprises (i) a peroxide selected from hydrogen peroxide and urea addition compounds thereof; (ii) a scavenger effective to remove heavy metals which may potentially decompose said peroxide catalytically; (iii) an alkaline buffer solution having the capacity to maintain the pH at a value within the range of 9.5 to 14; and (iv) an oxidizable substrate which comprises at least one compound selected from the group consisting of β-(3,4-dihydroxyphenyl)-α-alanine (DOPA), caffeic acid and salts thereof excepting heavy metal salts; and
    (b) observing whether within two hours from the contacting step an intense color develops indicating the presence of peroxidase-containing fungus in the sample; provided that said sample is a biological or clinical sample which has not been subjected to a culturing step prior to said contacting step.

2. A method according to claim 1, wherein said peroxide is selected from the group consisting of hydrogen peroxide and urea-hydrogen peroxide addition compound, said addition compound having a hydrogen peroxide content of approximately 35%.

3. A method according to claim 1, wherein said scavenger is ethylenediaminetetraacetic acid (EDTA) or a salt thereof.

4. A method according to claim 1, wherein said alkaline buffer solution is a 0.1M sodium carbonate-bicarbonate buffer solution.

5. A method according to claim 1, wherein there is used a mixture of 9 parts by volume 0.1M sodium carbonate-bicarbonate buffer solution as said alkaline buffer solution, with 1 part by volume 0.01M EDTA disodium salt solution, as said heavy metal scavenger.

6. The method of claim 1, wherein in step (b) said observation is made within 5 to 15 minutes from the contacting step.

7. A method for the detection of a peroxidase-containing fungus which comprises the steps of:
    (a) contacting a sample suspected of containing a peroxidase-containing fungus with a mixture which comprises (i) a peroxide selected from hydrogen peroxide and urea-hydrogen peroxide addition compound; (ii) a scavenger effective to remove heavy metals which may potentially decompose said peroxide catalytically; (iii) an alkaline buffer solution having the capacity to maintain the pH at a value within the range of 9.5 to 14; and (iv) an oxidizable substrate which comprises at least one compound selected from the group consisting of DOPA, caffeic acid and salts thereof excepting heavy metal salts; and
    (b) observing whether within two hours from the contacting step an intense color develops indicating the presence of peroxidase-containing fungus in the sample; and
    (c) in the case in which a color develops in step (b), stabilizing the color by lowering the pH to the 2.4 to 3.0 range; provided that said sample is a biological or clinical sample which has not been subjected to a culturing step prior to said contacting step.

8. A method according to claim 7, which also comprises the subsequent step of (d) comparing the intensity of the stabilized color with a predetermined scale for estimation of the presence and concentration of fungus in the sample.

9. A method according to claim 7, wherein said scavenger is ethylenediaminetetraacetic acid (EDTA) or a salt thereof.

10. A method according to claim 7, wherein said alkaline buffer solution is a 0.1M sodium carbonate-bicarbonate buffer solution.

11. A method according to claim 7, wherein there is used a mixture of 9 parts by volume 0.1M sodium carbonate-bicarbonate buffer solution as said alkaline buffer solution, with 1 part by volume 0.01M EDTA disodium salt solution, as said heavy metal scavenger.

12. A method according to claim 7, wherein said alkaline buffer is a sodium carbonate/sodium bicarbonate buffer and said pH within the range of 9.5 to 14 is substantially pH 10.

13. A method according to claim 7, wherein ingredients (ii) and (iii) are used in admixture.

14. A method according to claim 12, wherein ingredients (ii) and (iii) are used in admixture.

15. A method according to claim 7, wherein ingredient (ii) is EDTA disodium salt.

16. The method of claim 7, wherein in step (b) said observation is made within 5 to 15 minutes from the contacting step.

17. A test kit for use in a method for the detection of a peroxidase-containing fungus in a biological or clinical sample which has not been subjected to a culturing step prior to assay, the peroxidase being reactive at high alkaline pH, which test kit comprises the following components in containers:
   (A) a peroxide selected from hydrogen peroxide and urea addition compounds thereof;
   (B) a scavenger effective to remove heavy metals which may potentially decompose said peroxide catalytically;
   (C) an alkaline buffer solution having the capacity to maintain the pH at a value within the range of 9.5 to 14; and
   (D) an oxidizable substrate which comprises at least one compound selected from the group consisting of DOPA, caffeic acid and salts thereof excepting heavy metal salts.

18. A test kit according to claim 17 which comprises additionally at least one further component selected from (E), (F), (G) and (H), namely:
   (E) A substantially heavy metal-free acid component effective for lowering the pH of a test mixture which includes components (A), (B), (C) and (D), and a test specimen, to the 2.4 to 3.0 range;
   (F) a color scale for comparing any color which may be stabilized color which may be obtained in a test mixture which includes components (A), (B), (C), (D) and (E);
   (G) a sterile swab for collecting said test specimen; and
   (H) a test vessel adapted for mixing at least components (A), (B), (C), (D) and said test specimen.

19. A test kit for use in a method for the detection of a peroxidase-containing fungus in a biological or clinical sample which has not been subjected to a culturing step prior to assay, the peroxidase being reactive at high alkaline pH, which test kit comprises the following components in containers:
   (A) a peroxide selected from hydrogen peroxide and urea-hydrogen peroxide addition compound;
   (B) an EDTA-based scavenger effective to remove heavy metals which may potentially decompose said peroxide catalytically;
   (C) a sodium carbonate/sodium bicarbonate buffer solution having the capacity to maintain the pH at a value within the range of 9.5 to 14; and
   (D) an oxidizable substrate, which on reaction with oxygen at said pH value gives a visible intensely colored oxidation product, and wherein said substrate comprises at least one compound selected from the group consisting of DOPA, caffeic acid, and salts thereof excepting heavy metal salts.

20. A test kit according to claim 19 which comprises additionally at least one further component selected from (E), (F), (G) and (H), namely:
   (E) a substantially heavy metal-free acid component effective for lowering the pH of a test mixture which includes components (A), (B), (C) and (D), and a test specimen, to the 2.4 to 3.0 range;
   (F) a color scale for comparing any color which may be stabilized color which may be obtained in a test mixture which includes components (A), (B), (C), (D) and (E);
   (G) a sterile swab for collecting said test specimen; and
   (H) a test vessel adapted for mixing at least components (A), (B), (C), (D) and said test specimen.

21. A test kit according to claim 20, wherein component (E) comprises citric acid.

22. A test kit according to claim 17 provided that at least one of the conditions ($\alpha$) and ($\beta$) applies, namely
   ($\alpha$) components (B) and (C) are present in the form of a liquid phase admixture with each other;
   ($\beta$) components (A) and (D) are present in the form of a solid phase admixture with each other.

23. A test kit according to claim 22 which comprises additionally at least one further component selected from (E), (F), (G) and (H), namely:
   (E) a substantially heavy metal-free acid component effective for lowering the pH of a test mixture which includes components (A), (B), (C) and (D), and a test specimen, to the 2.4 to 3.0 range;
   (F) a color scale for comparing any color which may be stabilized color which may be obtained in a test mixture which includes components (A), (B), (C), (D) and (E);
   (G) a sterile swab for collecting said test specimen; and
   (H) a test vessel adapted for mixing at least components (A), (B), (C), (D) and said test specimen.

24. A test kit according to claim 22, wherein at least one of the following further conditions applies, namely: (1) component (A) is urea-hydrogen peroxide addition compound; (2) component (B) is an EDTA-based scavenger; and (3) component (C) is a sodium carbonate/sodium bicarbonate buffer solution having the capacity to maintain the pH at a value within the range of 9.5 to 14.

25. A test kit according to claim 23, wherein at least one of the following further conditions applies, namely: component (A) is urea-hydrogen peroxide addition compound; component (B) is an EDTA-based scavenger; and component (C) is a sodium carbonate/sodium bicarbonate buffer solution having the capacity to maintain the pH at a value within the range of 9.5 to 14.

26. A test kit according to claim 25, wherein component (E) comprises citric acid.

* * * * *